United States Patent
Martyres et al.

(10) Patent No.: US 7,759,365 B2
(45) Date of Patent: Jul. 20, 2010

(54) PIPERIDINE-SUBSTITUTED INDOLES

(75) Inventors: Domnic Martyres, Biberach (DE);
Pascale Pouzet, Biberach (DE);
Christoph Hoenke, Ingelheim (DE);
Peter Seither, Lustadt (DE); Silke Hobbie, Biberach (DE); Thierry Bouyssou, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 988 days.

(21) Appl. No.: 11/380,232

(22) Filed: Apr. 26, 2006

(65) Prior Publication Data

US 2006/0247230 A1 Nov. 2, 2006

(30) Foreign Application Priority Data

Apr. 30, 2005 (EP) ................... 05009556

(51) Int. Cl.
*A61K 31/454* (2006.01)
*C07D 403/14* (2006.01)

(52) U.S. Cl. ................... 514/323; 514/222.2; 544/3; 546/201

(58) Field of Classification Search ............. 514/222.2, 514/323; 544/3; 546/201
See application file for complete search history.

(56) References Cited

U.S. PATENT DOCUMENTS

| | | | | |
|---|---|---|---|---|
| 5,322,851 A | * | 6/1994 | Perregaard et al. | 514/323 |
| 5,462,948 A | * | 10/1995 | Perregaard et al. | 514/323 |
| 5,521,197 A | | 5/1996 | Audia | |
| 5,683,998 A | * | 11/1997 | Shibayama et al. | 514/218 |
| 5,846,982 A | * | 12/1998 | Audia et al. | 514/318 |
| 5,962,473 A | | 10/1999 | Johnson et al. | |
| 6,476,051 B2 | | 11/2002 | Mattson et al. | |
| 6,492,364 B1 | * | 12/2002 | Takahashi et al. | 514/243 |
| 6,602,889 B1 | * | 8/2003 | Perregaard et al. | 514/318 |
| 6,642,228 B1 | * | 11/2003 | Hayashi et al. | 514/230.5 |
| 6,683,096 B2 | | 1/2004 | Santacana et al. | |
| 6,743,809 B2 | | 6/2004 | Felding et al. | |
| 7,157,471 B2 | | 1/2007 | Anderskewitz et al. | |
| 7,544,806 B2 | * | 6/2009 | Anderskewitz et al. | 546/201 |
| 2004/0102450 A1 | | 5/2004 | Ewing et al. | |
| 2005/0153979 A1 | | 7/2005 | Anderskewitz et al. | |

FOREIGN PATENT DOCUMENTS

| WO | WO 98/02151 | 1/1998 |
|---|---|---|
| WO | WO 98/06402 | 2/1998 |
| WO | WO 98/11895 | 3/1998 |
| WO | WO 99/17773 | 4/1999 |
| WO | WO 99/37304 | 7/1999 |
| WO | WO 00/75130 A1 | 12/2000 |
| WO | WO 01/43740 A1 | 6/2001 |
| WO | WO 02/08223 A1 | 1/2002 |
| WO | 0214317 A2 | 2/2002 |
| WO | WO 03/070723 * | 8/2003 |
| WO | 03082867 A1 | 10/2003 |
| WO | 2005019203 A1 | 3/2005 |
| WO | 2005049559 A2 | 6/2005 |

OTHER PUBLICATIONS

Audia et al. "Preparation of piperidinyl . . . " Ca 130:52334 (1998).*
Balle et al. "Preparation of 5-heteroaryl . . . " CA 139:214476 (2003).*
Borbes et al. "CCR2B receptor . . . " Bioorg. med. Chem. Lett. v.10, p. 1803-1806 (2000).*
Ting et al. "The synthesis of substituted . . . " Bioorg. Med. chem. Lett. v. 15, p. 3020-3023 (2005).*
Exhibit i (2010).*
PCT form (2007).*
International Search Report, Form PCT/ISA/210, for corresponding PCT/EP2006/061839; mailed on Oct. 27, 2006.

* cited by examiner

*Primary Examiner*—Celia Chang
(74) *Attorney, Agent, or Firm*—Michael P. Morris; Mary-Ellen M. Devlin; Philip I. Datlow

(57) ABSTRACT

Disclosed are novel piperidine-substituted indoles- or hetero-derivatives thereof of the formula 1:

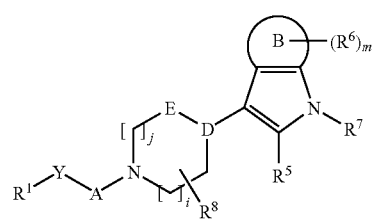

wherein $R^1$, $R^5$, $R^6$, $R^7$, A, B, D-E, Y, i, j, n and m are defined as below.

The compounds of formula 1 are useful as agonists or antagonists of CCR-3. The present invention is also directed to pharmaceutically acceptable salts thereof, more particularly to provide pharmaceutical compositions comprising a pharmaceutically acceptable carrier and a therapeutically effective amount of at least one of the compounds of the present invention or a pharmaceutically acceptable salt thereof.

14 Claims, No Drawings

PIPERIDINE-SUBSTITUTED INDOLES

BACKGROUND OF THE INVENTION

1. Technical Field

This invention relates generally to piperidine-substituted indoles- or heteroderivatives thereof and their use as modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

2. Background Information

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J Med., 338, 436-445 (1998) and Rollins, Blood, 90, 909-928 (1997)).

There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP2) and melanoma growth stimulatory activity protein (MGSA) are chemotactic primarily for neutrophils and T lymphocytes, whereas the CC chemokines, such as RANTES, MIP-Ia, MIP-1 (3, the monocyte chemotactic proteins (MCP-1, MCP-2, MCP-3, MCP-4, and MCP-5) and the eotaxins (−1, −2, and −3) are chemotactic for, among other cell types, macrophages, T lymphocytes, eosinophils, mast cells, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seventransmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, promotion of cell migration, survival and proliferation. There are at least ten human chemokine receptors that bind or respond to CC chemokines with the following characteristic patterns: CCR-1 (or "CKR-1" or "CC-CKR-1") [MIP-Ia, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B"or "CC-CKR-2A"/"CC-CKR-2B") [MCP-1, MCP2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-Ia, RANTES, MCP-1] (Power et al., J. Biol. Chem., 270, 19495-19500 (1995), Luster, New Eng. J. Med., 338, 436-445 (1998)); CCR-5 (or "CKR-5" OR "CCCKR-5") [MIP-Ia, RANTES, MIP-Ip] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1p] (Napolitano et al., J. Immunol., 157, 2759-2763 (1996), Bernardini et al., Eur. J. Immunol., 28, 582-588 (1998)); and CCR-10 (or "CKR-10" or "CC-CKR-10") [MCP-1, MCP-3] (Bonini et al, DNA and Cell Biol., 16, 1249-1256 (1997)).

In addition to the mammalian chemokine receptors, mammalian cytomegaloviruses, herpes viruses and poxviruses have been shown to express, in infected cells, proteins with the binding properties of chemokine receptors (reviewed by Wells and Schwartz, Curr. Opin. Biotech., 8, 741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR-4, CCR-2, CCR-3, CCR-5 and CCR-8, can act as coreceptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis, Grave's diesease and atherosclerosis. For example, the chemokine receptor CCR-3 is expressed among others on eosinophils, basophils, TH2 cells, alveolar macrophages, mast cells, epithelial cells, microglia cells, astrocytes and fibroblasts. CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR-3 expressing cells by HIV or in preventing the manipulation of immune cellular responses by viruses such as cytomegaloviruses.

Therefore, CCR-3 is an important target and antagonism of CCR-3 is likely to be effective in the treatment of inflammatory, immunoregulatory and infectious disorders and diseases.

BACKGROUND REFERENCES

U.S. Pat. No. 5,521,197 discloses piperidine-substituted indoles as 5-HT1F agonists.

The international patent application WO 98006402 discloses the use of these compounds for the treatment of cold or allergic rhinitis.

WO 98011895 discloses these compounds for the treatment of migraine.

Similar compounds are disclosed by WO 2001043740 also used as 5-HT modulators.

WO 2002008223 discloses piperidine-substituted indoles linked to peptide substituted aryl rings as D4 modulators, but also with partially effect at the 5-HT2A or the 5-HT2C receptor.

WO 99037304 discloses substituted piperidine- and piperazine-derivatives for the inhibition of the Factor $X_A$.

WO 2000075130 discloses indoylpiperidine derivatives as antihistaminic and antiallergic agents, what comprises the treatment of bronchial asthma.

The problem underlying the present invention was the provision of novel CCR-3 modulators, preferred with reduced side effects. It has been found surprisingly that certain piperidine-substituted indoles are highly suitable as CCR-3 modulators, having less side effects.

DETAILED DESCRIPTION OF THE INVENTION

The present invention relates to compounds of formula 1,

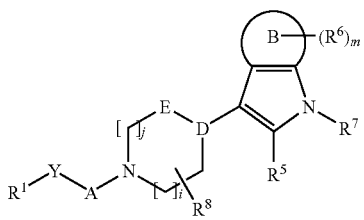

wherein
$R^1$ is aryl, het or a annelated species thereof, wherein het is a heterocyclic ring and the annelated species comprises aryl-het-, het-aryl- or het-het-annelations, each of said aryl or het may be substituted with one, two or three $R^2$;
$R^2$ are each independently $C_{1-6}$-alkyl, $C_{3-6}$-cycloalkyl, $C_{1-6}$-haloalkyl, $C_{6-10}$-aralkyl, halogen, CN, $COOR^3$, $COR^3$, $CONR^3R^4$, $NR^3R^4$, $NR^3SO_2R^4$, $OR^3$, $NO_2$, $SR^3$, $SOR^3$, $SO_2R^3$ or $SO_2NR^3R^4$;
$R^3$ is H, $C_{1-6}$-alkyl, $C_{3-8}$-cycloalkyl or (—$C_{3-8}$-cycloalkyl)-$C_{1-6}$-alkyl;
$R^4$ is H, $C_{1-6}$-alkyl, $C_{3-8}$-cycloalkyl or (—$C_{3-8}$-cycloalkyl)-$C_{1-6}$-alkyl or
$R^5$ is $C_{1-6}$-alkyl, $C_{1-6}$-alkoxy, $C_{1-6}$-acyloxy, $C_{6-10}$-aralkyl, $C_{3-6}$-cycloalkyl, ($C_{3-6}$-cycloalkyl)-$C_{1-6}$-alkyl, $C_{1-6}$-haloalkyl, $C_{1-6}$-thioalkyl, halogen, $NO_2$, CN, $NR^3R^4$;
$R^6$ are each independently $C_{1-6}$-alkyl, $C_{1-6}$-alkoxy, $C_{1-6}$-acyloxy, $C_{6-10}$-aralkyl, $C_{3-6}$-cycloalkyl, $C_{1-6}$-haloalkyl, $C_{1-6}$-thioalkyl, halogen, $OR^3$, $SR^3$, CN, $NO_2$, $COOR^3$, $COR^3$, $CONR^3R^4$, $NR^3R^4$, $NR^3COR^4$, $NR^3SO_2R^4$, $SOR^3$, $SO_2R^3$, $SO_2NR^3R^4$, aryl or het;
$R^7$ is H or a substituent selected from the group consisting of aryl and het, both optionally substituted with one, two, three or four substituents selected from the group consisting of H, $COOR^{7.1}$, $SO_2R^{7.1}$, halogen, OH, O—$C_{1-6}$-alkyl, CN, $PO(OH)_2$, CONHCN, $SO_2NHCOR^{7.1}$, $SO_2NHR^{7.1}$ and $R^{7.2}$;
$R^{7.1}$ is H, $C_{1-6}$-alkyl or aryl;
$R^{7.2}$ is a five or six-membered, aromatic or nonaromatic heterocyclic ring containing one, two, three or four atoms selected from the group consisting of nitrogen, sulfur and oxygen, optionally substituted by one, two or three oxo;
$R^8$ is H, OH, $C_{1-6}$-alkoxy, $C_{1-6}$-haloalkyl, halogen;
$R^9$ is H, OH, $C_{1-6}$-alkoxy, $C_{1-6}$-haloalkyl, halogen;
A is straight, branched or cyclic $C_{2-8}$-alkylen; optionally substituted with $R^9$
B is aryl or het;
D-E is —CH—$CH_2$—, —C=CH—, —$CR^8$—$CH_2$—;
Y is —$CH_2$—, —$NR^4$—, —O—, —$S(O)_n$—;
i, j are each independently 0, 1 or 2, wherein $0 \leq i+j \leq 4$;
n is 0, 1 or 2;
m is 0, 1, 2, 3 or 4;

and pharmaceutically acceptable salts thereof, with the provisio that both $R^7$ and $R^8$ cannot have the meaning of hydrogen at the same time.

The compounds herein described may have asymmetric centres. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The term "substituted" as used herein, means that any one or more hydrogens on the designated atom is replaced with a selection from the indicated group, provided that the designated atom's normal valence is not exceeded, and that the substitution results in a stable compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isothionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remingto which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a carboxylic acid, hydroxy, amino, or sulfhydryl group is bonded to any group that, when the prodrug of the present invention is administered to a mammalian subject, it cleaves to form a free carboxylic acid, hydroxyl, free amino, or free sulfhydryl group, respectively. Examples of prodrugs include, but are not limited to, acetate, formate and benzoate derivatives of alcohol and amine functional groups in the compounds of the present invention.

The term "aryl" as used herein, either alone or in combination with another substituent, means either an aromatic monocyclic system or aromatic multicyclic systems containing carbon atoms. For example, aryl includes a phenyl or a naphthyl ring system, wherein aryl means generally an aromatic system, for example phenyl.

The term "het" as used herein, either alone or in combination with another substituent, means a monovalent substituent derived by removal of a hydrogen from a five-, six- or seven-membered saturated or unsaturated (including aromatic) heterocycle containing carbon atoms and one, two, three or four ring heteroatoms selected from nitrogen, oxygen and sulfur. Examples of suitable heterocycles include: tetrahydrofuran, thiophene, diazepine, isoxazole, piperidine, dioxane, morpholine, piperazine or

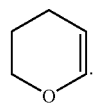

Although generally covered under the term "het", the term "heteroaryl" as used herein precisely defines an unsaturated heterocycle for which the double bonds form an aromatic system. Suitable example of heteroaromatic system include:

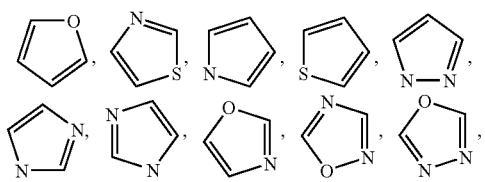

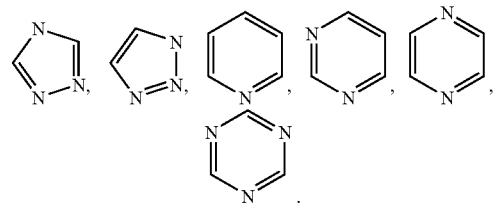

The term "annelated species of aryl or het" as used herein, either alone or in combination with another substituent wherein the annelated species presents as a aryl-het (a), a het-aryl (b) or a het-het (c) annelation means a monovalent substituent derived by removal of one hydrogen from an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of a annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "$C_{1-6}$-alkyl" as used herein, either alone or in combination with another substituent, means acyclic, straight or branched chain alkyl substituents containing from one to six carbon atoms and includes, for example, methyl, ethyl, propyl, butyl, hexyl, 1-methylethyl, 1-methylpropyl, 2-methylpropyl or 1,1-dimethylethyl.

The term "$C_{3-8}$-cycloalkyl" as used herein, either alone or in combination with another substituent, means a cycloalkyl substituent containing from three to six carbon atoms and includes cyclopropyl, cyclobutyl, cyclopentyl or cyclohexyl.

The term "$C_{1-6}$-haloalkyl" as used herein, either alone or in combination with another substituent, means acyclic, straight or branched chain alkyl substituents containing up to six carbon atoms having one or more hydrogens substituted for a halogen selected from bromo, chloro, fluoro or iodo. Accordingly "$C_{2-6}$-haloalkyl" has the same meaning with exception that the chain contains two to six carbon atoms. Preferably the term $C_{1-6}$-haloalkyl represents $C_{1-6}$-fluoroalkyl such as trifluoromethyl, 2,2,2-trifluoroethyl or perfluoroethyl.

The term "$C_{1-6}$-alkoxy" as used herein, either alone or in combination with another substituent, means the substituent $C_{1-6}$-alkyl-O— wherein alkyl is as defined above containing up to six carbon atoms. Alkoxy includes methoxy, ethoxy, propoxy, 1-methyl-ethoxy, butoxy or 1,1-dimethylethoxy. The latter substituent is known commonly as t-butoxy.

The term "$C_{1-6}$-acyloxy" as used herein, either alone or in combination with another substituent, means the substituent $C_{1-6}$-alkyl-(CO)O— wherein alkyl is as defined above containing up to six carbon atoms. Acyloxy includes MeCOO—, EtCOO—, $^n$PrCOO—, $^i$PrCOO—, $^n$BuCOO—, $^{sec}$BuCOO— or $^t$BuCOO—.

The term "$C_{6-10}$-aralkyl" as used herein, either alone or in combination with another substituent, means the substituent ($C_{1-4}$-alkyl)-Aryl wherein alkyl is as defined above containing up to six carbon atoms. Aralkyl includes benzyl, phenylethyl, phenylpropyl, 1-phenyl-1-methylethyl, phenylbutyl or 1-phenyl-1,1-dimethylethyl.

The term "$C_{1-6}$-thioalkyl" as used herein, either alone or in combination with another substituent, means acyclic, straight or branched chain alkyl substituents containing up to six carbon atoms and a thiol (HS) group as a substituent. An example of a thioalkyl group is a thiopropyl, e.g., HS—$CH_2CH_2CH_2$—.

The term "$C_{2-8}$-alkylene" as used herein means a divalent alkyl substituent derived by the removal of one hydrogen atom from each end of a saturated straight or branched chain aliphatic hydrocarbon containing from two to eight carbon atoms and includes, for example, —$CH_2CH_2C(CH_3)_2CH_2CH_2$—. Accordingly "$C_{1-3}$-alkylene" has the same meaning with exception that the chain contains one to three carbon atoms. If mentioned the aliphatic chain can also containing a cyclic groups e.g.

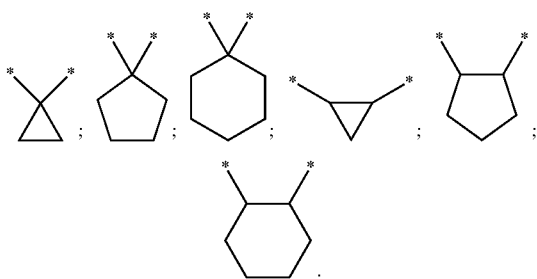

The partial formula

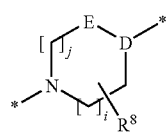

represents a cyclic group in which one or two hydrogen atoms may be replaced by the group $R^8$. Preferred are the following cyclic groups:

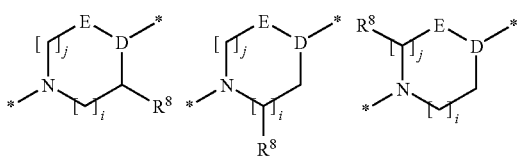

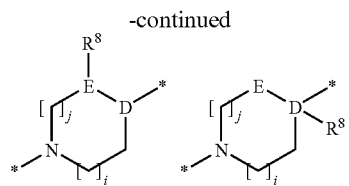

Preferred Embodiments

Preferred are compounds of formula 1, wherein Y is —$NR^4$—, —O— or —S(O)$_n$—, preferred —$NR^4$— or —S—, and $R^1$, $R^5$, $R^6$, $R^7$, $R^8$, A, B, D-E, i, j, n and m are defined as above. Particularly preferred are compounds of formula 1a,

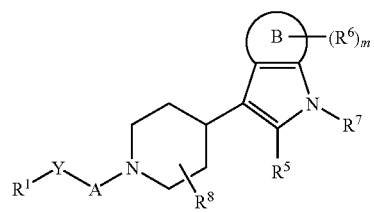

1a wherein $R^1$, $R^5$, $R^6$, $R^7$, $R^8$, A, B, Y and m are defined as above.

Also preferred are compounds of the formula 1 or 1a wherein:
$R^5$ is $C_{1-6}$-alkyl, $C_{1-6}$-alkoxy, $C_{1-6}$-acyloxy, $C_{6-10}$-aralkyl, $C_{3-6}$-cycloalkyl, ($C_{3-6}$-cycloalkyl)-$C_{1-6}$-alkyl, $C_{1-6}$-haloalkyl, $C_{1-6}$-thioalkyl, halogen, $NO_2$, CN;

Also preferred are compounds of the formula 1 or 1a wherein:
$R^1$ is aryl or het, both optionally substituted with one, two or three $R^2$ and
B is phenyl.

Also preferred are compounds of the formula 1 or 1a wherein:
$R^1$ is phenyl, optionally substituted with one, two or three $R^2$ and
B is phenyl.

Also preferred are compounds of the formula 1 or 1a wherein:
$R^1$ is phenyl, optionally substituted with one, two or three $R^2$ and
B is phenyl and
$R^8$ is H.

Also preferred are compounds of the formula 1 or 1a wherein:
$R^1$ is phenyl, optionally substituted with one, two or three $R^2$ and
B is phenyl and
$R^8$ is OH, $C_{1-6}$-alkoxy, $C_{1-6}$-haloalkyl, halogen.
A is —$CH_2$—$CH_2$—$CH_2$—.

Also preferred are compounds of the formula 1 or 1a wherein:
$R^1$ is phenyl, optionally substituted with one, two or three $R^2$ and
B is phenyl and
$R^8$ is H and
A is —$CH_2$—$CH_2$—$CH_2$—.

Also preferred are compounds of the formula 1 or 1a wherein:
$R^7$ is H; and
$R^8$ is OH, $C_{1-6}$-alkoxy, $C_{1-6}$-haloalkyl, halogen.

Also preferred are compounds of the formula 1 or 1a wherein:
$R^7$ is aryl and het, both optionally substituted with one, two, three or four substituents selected from the group consisting of H, $COOR^{7.1}$, $SO_2R^{7.1}$, halogen, OH, $C_{1-6}$-alkoxy, CN, $PO(OH)_2$, CONHCN, $SO_2NHCOR^{7.1}$, $SO_2NHR^{7.1}$ and $R^{7.2}$;
$R^{7.1}$ is H, $C_{1-6}$-alkyl or aryl;
$R^{7.2}$ is a five or six-membered, aromatic or nonaromatic heterocyclic ring containing one, two, three or four atoms selected from the group consisting of nitrogen, sulfur and oxygen, optionally substituted by one, two or three oxo and
$R^8$ is OH, $C_{1-6}$-alkoxy, $C_{1-6}$-haloalkyl, halogen.

Also preferred are compounds of the formula 1 or 1a wherein:
$R^7$ is aryl and het, both optionally substituted with one, two, three or four substituents selected from the group consisting of H, $COOR^{7.1}$, $SO_2R^{7.1}$, halogen, OH, $C_{1-6}$-alkoxy, CN, $PO(OH)_2$, CONHCN, $SO_2NHCOR^{7.1}$, $SO_2NHR^{7.1}$ and $R^{7.2}$;
$R^{7.1}$ is H, $C_{1-6}$-alkyl or aryl;
$R^{7.2}$ is a five or six-membered, aromatic or nonaromatic heterocyclic ring containing one, two, three or four atoms selected from the group consisting of nitrogen, sulfur and oxygen, optionally substituted by one, two or three oxo; and
$R^8$ H.

Also preferred are compounds of the formula 1 or 1a wherein:
$R^7$ is H or a substituent selected from the group consisting of aryl and het, both optionally substituted with one, two, three or four substituents selected from the group consisting of H, $COOR^{7.1}$, $SO_2R^{7.1}$, halogen, OH, $C_{1-6}$-alkoxy, CN, $PO(OH)_2$, CONHCN, $SO_2NHCOR^{7.1}$, $SO_2NHR^{7.1}$ and $R^{7.2}$;
$R^{7.1}$ is H, $C_{1-6}$-alkyl or aryl;
$R^{7.2}$ is a substituent selected from

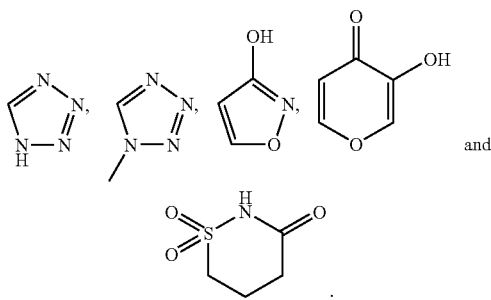

Also preferred are compounds of the formula 1 or 1a wherein:
$R^5$ is —$C_{1-6}$-alkyl, $C_{3-6}$-cycloalkyl, $C_{2-6}$-haloalkyl.

Also preferred are compounds of the formula 1 or 1a wherein:
$R^7$ is aryl, optionally substituted with one, two, three or four substituents selected from the group consiting of H, $COOR^{7.1}$, $SO_2R^{7.1}$, OH, CN, $PO(OH)_2$, CONHCN, $SO_2NHCOH$, $SO_2NH_2$ and tetrazole;
$R^{7.1}$ H, $C_{1-6}$-alkyl, aryl.

Also preferred is the process for preparing compounds of formula 1 or 1a characterised in that a compound of formula 2

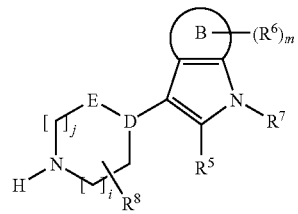

is reacted with a compound of the formula 3.

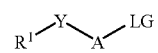

wherein $R^1$, $R^5$, $R^6$, $R^7$, A, B, j and m are defined as above and LG is a suitable leaving group, in particular halogen, mesylate, triflate, tosylate or brosylate.

The compounds of formula 1 or 1a can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1991).

The compounds of the instant application are useful for manufacturing a medicament for the prevention and/or treatment of diseases wherein the activity of a CCR-3-receptor is involved.

Preferred is the manufacturing of a medicament for the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

Most preferred is the manufacturing of a medicament for the prevention and/or treatment of e.g. inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs.

Preparation

Carbon substituted compounds of the formula 2c or 2d are prepared by a C—C coupling reaction under Buchwald conditions of a ring B, substituted at least by one nitro-function and a halogen in ortho-position, with a α-C-atom of a keto function,

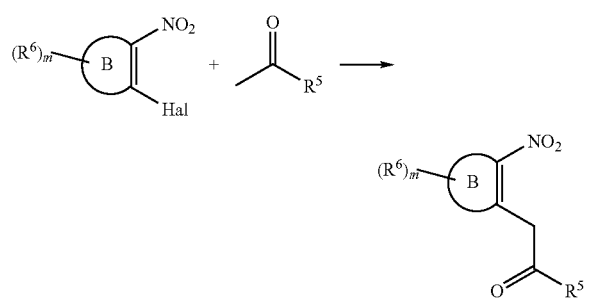

(Hal represents Cl or Br) after the coupling reaction a ring closure under reductive conditions is promoted,

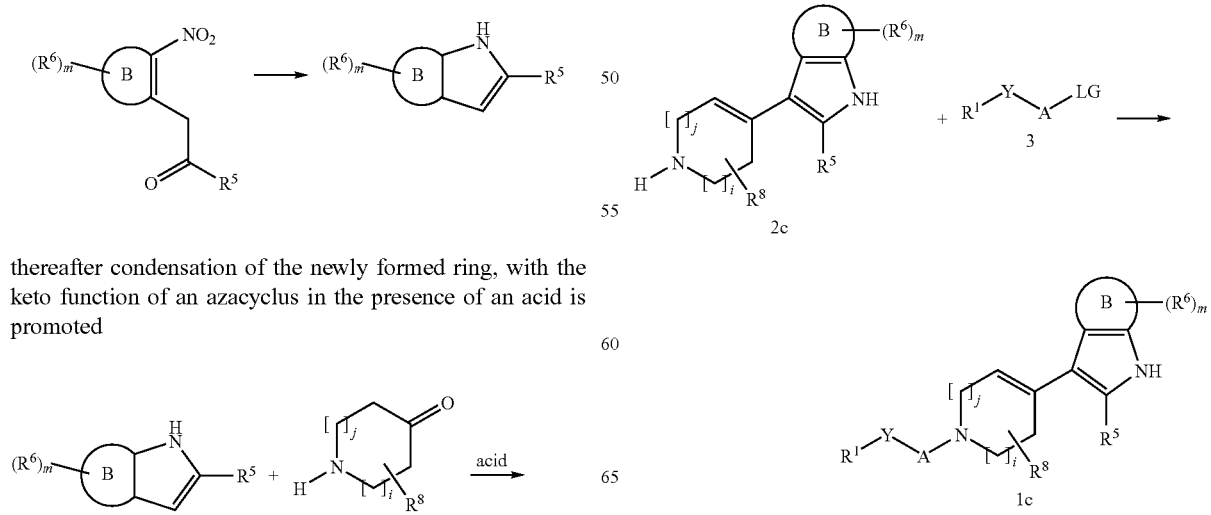

thereafter condensation of the newly formed ring, with the keto function of an azacyclus in the presence of an acid is promoted

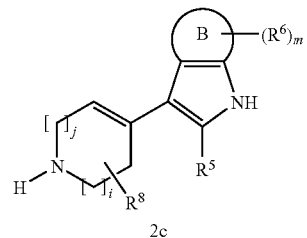

followed by, in the case of compounds 2d, with hydrogenation of the double bond of the azacyclus wherein the whole process $R^5$, $R^6$, B, D-E, i, j and m are defined as above Compounds of the formulae 1c-d can be prepared by reacting compounds 2b-d with a compound of formula 3

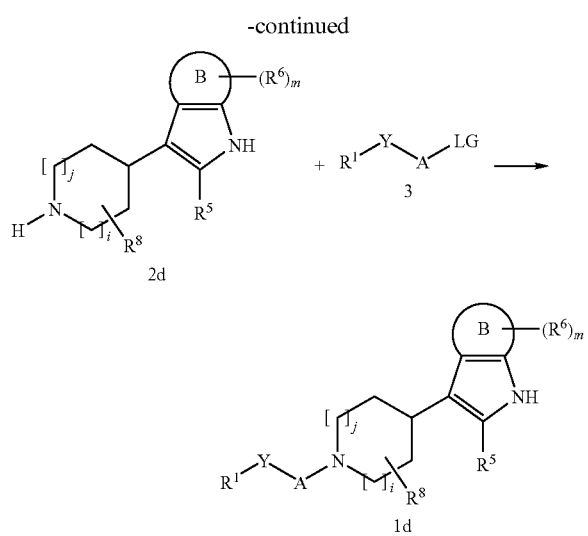

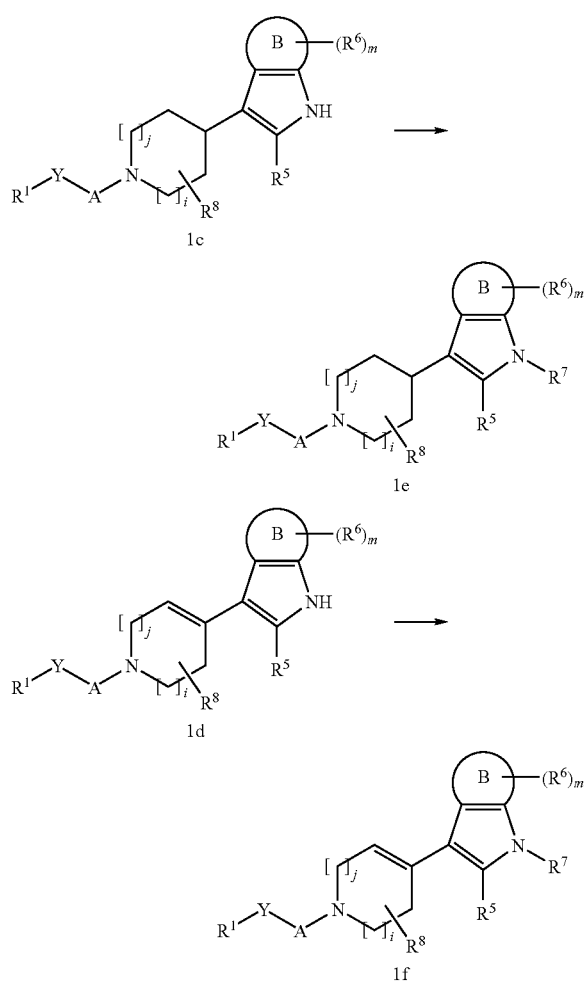

wherein $R^1$, $R^5$, $R^6$, A, B, Y, i, j and m are defined as above; and LG is a suitable leaving group, in particular halogen, mesylate, triflate, tosylate or brosylate.

N-substituted species of the formulae 1e or 1f can be prepared by reacting compounds 1c or 1d.

wherein $R^1$, $R^5$, $R^6$, $R^7$ A, B, Y, i, j and m are defined as above. Compounds 1e or 1f can also be obtained by N-substitution of 2c or 2d and coupling the reaction products with compound 3.

As will be appreciated by one of skill in the art, numerous modifications and variations of the present invention are possible in light of the above teachings. It is therefore to be understood that within the scope of the appended claims, the invention may be practiced otherwise than as specifically described herein.

EXAMPLE 1

1-(3-BROMO-PROPYLSULFANYL)-4-FLUORO-BENZENE

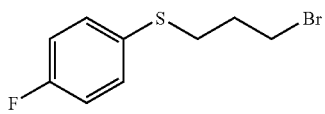

To a solution of p-fluoro-thiophenole (20.8 ml) and 1-3-dibromopropane (60 ml) in acetonitrile (250 ml) is added $K_2CO_3$ (55.0 g) in small quantities and the mixture refluxed for 3 hours. Thereafter the resulting salt and solvent are removed and the product distilled. Bp.112-115° C./1 mbar.

EXAMPLE 2

1-(2-NITRO-4-FLUORO-PHENYL)-BUTAN-2-ONE

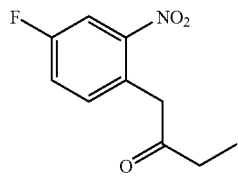

To a solution of 1-bromo-2-nitro-4-fluoro-phenyl (6.2 g), $Pd_2$ $dba_3$ (260 mg), 2-dicyclohexylphosphino-2'-(N,N-dimethylamino)biphenyl (455 mg), $K_3PO_4$ (13.7 g) and 4-Methoxyphenol (700 mg) in toluene (60 ml) is added 2-butanone (5.6 ml) and the reaction mixture heated up to 60° C. for 24 hours under Argon. Thereafter the mixture is extracted with water and ethyl acetate (1:1), and washed with a 2M NaOH solution and water. The solvent is removed and the remaining product purified by flash chromatography (9:1 cyclohexene: ethyl acetate) to give 2.6 g (44%) of pure product as light yellow crystals.

$^1$H NMR (400 MHz, DMSO): 0.98 (3H, t), 2.56 (2H, q), 4.22 (2H, s), 7.51 (1H, dd), 7.63 (1H, td), 7.98 (1H, dd).

EXAMPLE 3

2-ETHYL-6-FLUORO-1H-INDOLE

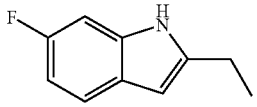

A solution of 1-(2-nitro-3-fluoro-phenyl)-butan-2-one (2.5 g) in ethanol (25 ml) is heated to 70° C. $Na_2S_2O_4$ (10.7 g) in water (30 ml) is added and the resulting mixture heated under reflux for 1 hour. The ethanol is removed by distillation, the residue extracted twice with ethyl acetate, the organic layer then washed with water and dried. The solvent is removed and the remaining product freed from impurities by flash chromatography (9:1 cyclohexane:ethyl acetate). 1.3 g (67%) of pure product is obtained as a white crystalline solid.

$^1$H NMR (400 MHz, DMSO): 1.26 (3H, t), 2.72 (2H, q), 6.12 (1H, s), 6.73-6.80 (1H, m), 7.02 (1H, br d), 7.37 (1H, dd), 10.98 (1H, br s).

EXAMPLE 4

2-ETHYL-6-FLUORO-3-(1,2,3,6-TETRAHYDRO-PYRIDIN-4-YL)-1H-INDOLE

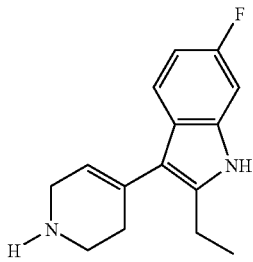

To a suspension of 2-ethyl-5-fluoro-1H-indole (1.2 g) in acetic acid (21 ml) at 90° C. is added a mixture of 4-piperidone (3.4 g) and 2N phosphoric acid (7 ml). The reaction mixture is stirred at 95° C. for 4 h, then water (50 ml) is added and the reaction allowed to cool to rt. The pH is adjusted to 11 with conc. NaOH solution and the mixture extracted into ethyl acetate. This is washed with water, dried over magnesium sulphate and concentrated in vacuo. The product is washed (ether) and dried over a suction filter, to give 1.5 g (84%) of product as a white crystalline solid. Mp. 194-6° C.

EXAMPLE 5

2-ETHYL-6-FLUORO-3-PIPERIDIN-4-YL-1H—INDOLE

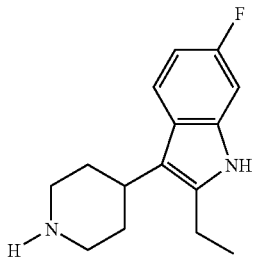

3-(1-Benzyl-1,2,3,6-tetrahydro-pyridin-4-yl)-2-ethyl-6-fluoro-1H-indole (1.4 g) is hydro-genated for 1 hour (r.t./1013 mbar) in the presence of 10% Pd/C catalyst (0.3 g) and methanol (25 ml). The catalyst is removed by filtration, the solvent evaporated and the residue washed with small portions of ether. 1.2 g (85%) of pure product is obtained.

$^1$H NMR (400 MHz, DMSO): 1.20 (3H, t), 1.52 (2H, br d), 1.90-2.04 (2H, m), 2.59-2.71 (4H, m), 2.71-2.83 (1H, m), 3.07 (2H, br d), 6.74 (1H, t), 6.99 (1H, d), 7.52-7.60 (1H, m), 10.72 (1H, br s).

EXAMPLE 6

2-ETHYL-6-FLUORO-3-{1-[3-(4-FLUORO-PHENYLSULFANYL)-PROPYL]-PIPERIDIN-4-YL}-1H-INDOLE

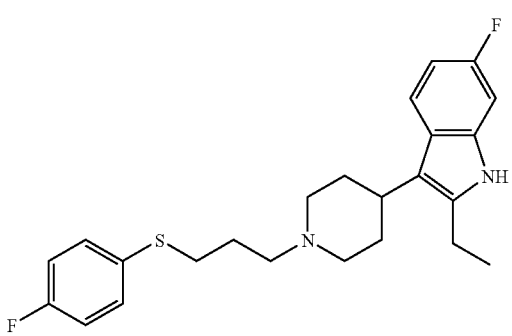

A mixture of 2-ethyl-6-fluoro-3-piperidin-4-yl-1H-indole (0.9 g), 1-(3-Bromo-propylsulfanyl)-4-fluoro-benzene (1.0 g), potassium iodide (20 mg) and potassium carbonate (0.7 g) in DMF (10 ml) is heated at 100° C. for 3 h, and allowed to cool to rt overnight. Ethyl acetate (50 ml) and water (25 ml) are added and the organic phase is washed with water, dried and concentrated in vacuo. The crude product is purified by flash chromatography (95:5 $CH_2Cl_2$:MeOH) and its hydrochloride salt is prepared by reaction in acetone with the appropriate amount of ethereal HCl giving, after recrystallisation from ether, 1.1 g pure product (70%) as white crystals.

$^1$H NMR (400 MHz, DMSO): 1.19 (3H, t), 1.75 (2H, br d), 1.92-2.02 (2H, m), 2.35 (2H, br q), 2.59 (2H, q), 2.92-3.09 (5H, m), 3.10-3.20 (2H, m), 3.47 (2H, br d), 6.71-6.79 (1H, m), 7.01 (1H, dd), 7.22 (2H, br t), 7.44-7.49 (2H, m), 7.58-7.62 (1H, m), 10.87 (1H, br s).

EXAMPLE 6B

4-(2-ETHYL-6-FLUORO-1H-INDOL-3-YL)-PIPERIDINE-1-CARBOXYLIC ACID TERT-BUTYL ESTER

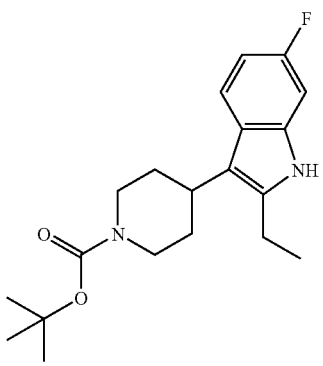

To a stirred solution of 2-ethyl-6-fluoro-3-piperidin-4-yl-1H-indole (1.3 g) in DCM (50 ml) at r.t., is added triethylamine (2.2 ml) and BOC-anhydride (1.27 g). After 15 h, the mixture is washed with water and the organic phase concentrated in vacuo giving 70 mg pure product (57%) as a light brown solid. R.f. (7:3 cyclohexane:ethyl acetate) 0.5.

EXAMPLE 7

4-(2-ETHYL-6-FLUORO-1-PHENYL-1H-INDOL-3-YL)-PIPERIDINE-1-CARBOXYLIC ACID TERT-BUTYL ESTER

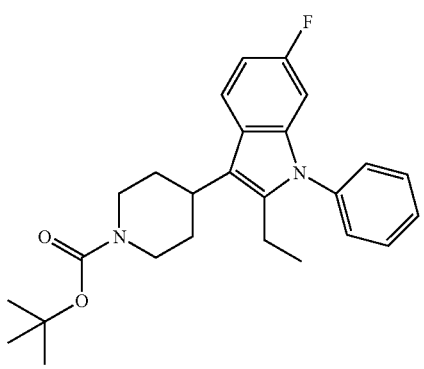

To a solution of 4-(2-ethyl-6-fluoro-1H-indol-3-yl)piperidine-1-carboxylic acid tert-butyl ester (0.36 g) in degassed toluene (10 ml) at r.t., is added potassium phosphate (0.1 g), copper iodide (20 mg), iodobenzene (254 mg) and N,N'-dimethylcyclohexane-1,2-diamine (30 mg). The mixture is heated at reflux for 3 days. Thereafter the mixture is allowed to cool to r.t., and water (20 ml) added. Ethyl acetate (3×10 ml) is used to extract the organic components and the organic layer is washed with water, dried over MgSO$_4$ and concentrated in vacuo. Flash chromatography (9:1 cyclohexane: ethyl acetate) gives 120 mg pure product (27%) as a brown solid.

All other couplings were performed similary. If iodoaryls were not available purchaseable bromoaryls were converted to iodoaryls according to J. Am. Chem. Soc. 2002, 124, 14844-14845.

EXAMPLE 8

2-ETHYL-6-FLUORO-1-PHENYL-3-PIPERIDIN-4-YL-1H-INDOLE

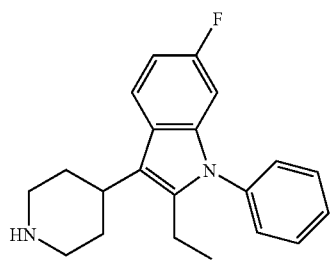

To a stirred solution of 4-(2-ethyl-6-fluoro-1-phenyl-1H-indol-3-yl)-piperidine-1-carboxylic acid tert-butyl ester (0.12 g) in DCM (20 ml) at r.t., is added trifluoroacetic acid (0.5 ml). After 15 h, the mixture is concentrated in vacuo. Flash chromatography (DCM:MeOH, gradient elution) of the resulting liquid gives 70 mg pure product (57%, TFA salt) as a beige solid after trituration with diethylether.

EXAMPLE 9

2-ETHYL-6-FLUORO-3-{1-[3-(4-FLUOROPHE-NYLSULFANYL)-PROPYL]-PIPERIDIN-4-YL}-1-PHENYL-1H-INDOLE

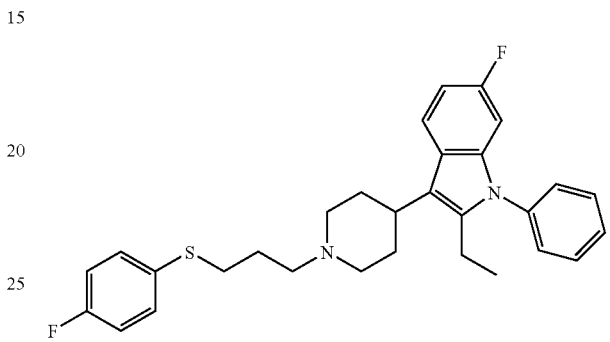

A mixture of 2-ethyl-6-fluoro-1-phenyl-3-piperidin-4-yl-1H-indole (70 mg, TFA salt), 1-(3-Bromo-propylsulfanyl)-4-fluoro-benzene (44 mg), potassium iodide (5 mg) and potassium carbonate (55 mg) in DMF (3 ml) is heated at 80° C. for 3 h, and allowed to cool to r.t. overnight. Ethyl acetate (50 ml) and water (25 ml) are added and the organic phase is washed with water, dried and concentrated in vacuo. The crude product is purified by flash chromatography (98:2 CH$_2$Cl$_2$: MeOH) to give 50 mg pure product (64%) as brown solid.

EXAMPLE 10

4-(2-ETHYL-6-FLUORO-3-{1-[3-(4-FLUORO-PHENYLSULFANYL)-PROPYL]-PIPERIDIN-4-YL}-INDOL-1-YL)-BENZOIC ACID ETHYL ESTER

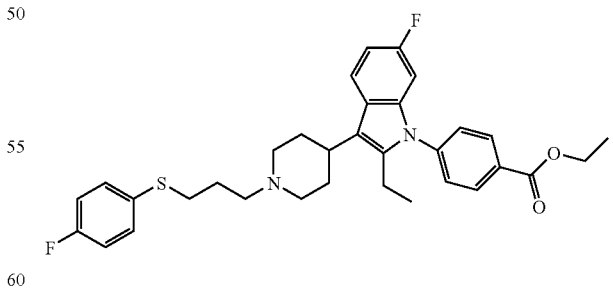

To a mixture of 2-ethyl-6-fluoro-3-{1-[3-(4-fluoro-phenylsulfanyl)-propyl]-piperidin-4-yl}-1H-indole (430 mg), p-iodobenzoic acid ethyl ester (716 mg), potassium carbonate (359 mg), copper iodide (52 mg) and zinc oxide (14 mg) in a reactor vial under argon is added NMP (3 ml) and the reaction heated by microwaves irradiation at 160° C. After 120 min, water is added and the suspension extracted with DCM. Preparative HPLC provides 150 mg pure product (26%) as a beige solid. R.t. 4.81 min.

EXAMPLE 11

4-(2-ETHYL-6-FLUORO-3-{1-[3-(4-FLUORO-PHENYLSULFANYL)-PROPYL]-PIPERIDIN-4-YL}-INDOL-1-YL)-BENZOIC ACID

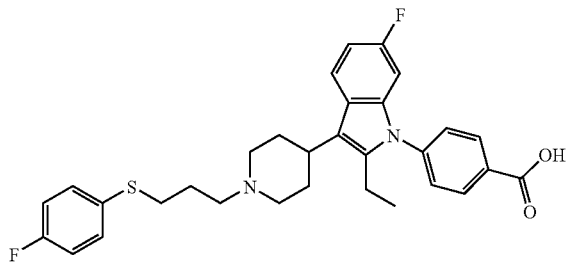

To a solution of 4-(2-ethyl-6-fluoro-3-{1-[3-(4-fluoro-phenylsulfanyl)-propyl]-piperidinn-4-yl}-indol-1-yl)-benzoic acid ethyl ester (150 mg), in ethanol (5 ml) is added NaOH (2M, 1 ml) and the reaction heated to reflux. After 2 h, the reaction is allowed to cool to r.t. and made slightly acidic with HCl (aq, 2M). Ethyl acetate is added resulting in precipitation of the product which is filtered resulting in 38 mg pure product (27%) as a beige solid.

$^1$H NMR (400 MHz, DMSO): 0.89 (3H, t), 1.65-1.72 (2H, m), 1.72-1.82 (2H, m), 2.05-2.22 (4H, m), 2.60-2.71 (2H, m), 2.75-2.84 (1H, m), 2.93-3.05 (4H, m), 3.22-3.40 (2H, m, obscured by residual solvent peak), 6.71 (1H, d), 6.89 (1H, td), 7.19 (2H, t), 7.42 (2H, dd), 7.51 (2H, d), 7.68 (1H, dd), 8.11 (2H, d).

The following examples can be synthesised according to the above mentioned synthetic routes.

TABLE 1

Examples according to formula EX1:

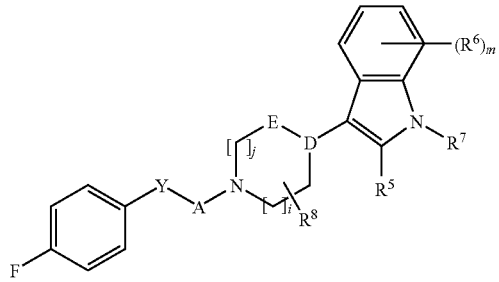

EX1

| # | A | D—E | i | j | m | Y | $R^5$ | $R^6$ | $R^7$ | $R^8$ |
|---|---|---|---|---|---|---|---|---|---|---|
| 12. | CH$_2$CH$_2$CH$_2$ | CH—CH$_2$ | 1 | 1 | 1 | S | i-Pr | 6-F | p-benzoic acid ethyl ester | H |
| 13. | CH$_2$CH$_2$CH$_2$ | CH—CH$_2$ | 1 | 1 | 1 | S | i-Pr | 6-F | p-benzoic acid | H |
| 14. | CH$_2$CH$_2$CH$_2$ | CH—CH$_2$ | 1 | 1 | 1 | S | sec-Bu | 6-F | p-benzoic acid ethyl ester | H |
| 15. | CH$_2$CH$_2$CH$_2$ | CH—CH$_2$ | 1 | 1 | 1 | S | sec-Bu | 6-F | p-benzoic acid | H |
| 16. | CH$_2$CH$_2$CH$_2$ | CH—CH$_2$ | 1 | 1 | 1 | S | c-Pr | 6-F | p-benzoic acid ethyl ester | H |
| 17. | CH$_2$CH$_2$CH$_2$ | CH—CH$_2$ | 1 | 1 | 1 | S | c-Pr | 6-F | p-benzoic acid | H |
| 18. | CH$_2$CH$_2$CH$_2$ | CH—CH$_2$ | 1 | 1 | 1 | S | c-Bu | 6-F | p-benzoic acid ethyl ester | H |
| 19. | CH$_2$CH$_2$CH$_2$ | CH—CH$_2$ | 1 | 1 | 1 | S | c-Bu | 6-F | p-benzoic acid | H |
| 20. | CH$_2$CH$_2$CH$_2$ | CH—CH$_2$ | 1 | 1 | 1 | S | Et | 6-F | p-benzonitrile | H |
| 21. | CH$_2$CH$_2$CH$_2$ | CH—CH$_2$ | 1 | 1 | 1 | S | Et | 6-F | p-phenyltetrazole | H |
| 22. | CH$_2$CH$_2$CH$_2$ | CH—CH$_2$ | 1 | 1 | 1 | S | Et | 6-F | N-methyl-phenyltetrazole | H |
| 23. | CH$_2$CH$_2$CH$_2$ | CH—CH$_2$ | 1 | 1 | 1 | S | Et | 6-F | m-benzoic acid ethyl ester | H |
| 24. | CH$_2$CH$_2$CH$_2$ | CH—CH$_2$ | 1 | 1 | 1 | S | Et | 6-F | m-benzoic acid | H |
| 25. | CH$_2$CH$_2$CH$_2$ | CH—CH$_2$ | 1 | 1 | 1 | S | Et | 6-F | o-benzoic acid ethyl ester | H |
| 26. | CH$_2$CH$_2$CH$_2$ | CH—CH$_2$ | 1 | 1 | 1 | S | Et | 6-F | o-benzoic acid | H |
| 27. | CH$_2$CH$_2$CH$_2$ | CH—CH$_2$ | 1 | 1 | 1 | S | Et | 6-CO2H | phenyl | H |
| 28. | CH$_2$CH$_2$CH$_2$ | CH—CH$_2$ | 1 | 1 | 1 | S | Et | 6-CN | p-benzoic acid ethyl ester | H |
| 29. | CH$_2$CH$_2$CH$_2$ | CH—CH$_2$ | 1 | 1 | 1 | S | Et | 6-C(O)NH2 | p-benzoic acid ethyl ester | H |
| 30. | CH$_2$CH$_2$CH$_2$ | CH—CH$_2$ | 1 | 1 | 1 | S | Et | 6-OH | p-benzoic acid ethyl ester | H |
| 31. | CH$_2$CH$_2$CH$_2$ | CH—CH$_2$ | 1 | 1 | 1 | S | Et | 6-CN | p-benzoic acid | H |
| 32. | CH$_2$CH$_2$CH$_2$ | CH—CH$_2$ | 1 | 1 | 1 | S | Et | 6-C(O)NH2 | p-benzoic acid | H |
| 33. | CH$_2$CH$_2$CH$_2$ | CH—CH$_2$ | 1 | 1 | 1 | S | Et | 6-OH | p-benzoic acid | H |
| 34. | CH$_2$CH$_2$CH$_2$ | CH—CH$_2$ | 1 | 1 | 1 | S | Et | 6-F | benzene sulfinic acid amide* | H |
| 35. | CH$_2$CH$_2$CH$_2$ | CH—CH$_2$ | 1 | 1 | 1 | S | Et | 6-F | p-N-methyl benzene sulfonamide | H |
| 36. | CH$_2$CH$_2$CH$_2$ | CH—CH$_2$ | 1 | 1 | 1 | S | Et | 6-F | benzene sulfonamide | H |
| 37. | CH$_2$CH$_2$CH$_2$ | CH—CH$_2$ | 1 | 1 | 1 | S | Et | 6-F | N,N-di-Me-benzene sulfinic acid amide | H |
| 38. | CH$_2$CH$_2$CH$_2$ | CH—CH$_2$ | 1 | 1 | 1 | S | Et | 6-F | N,N-di-Me-benzene sulfonamide | H |
| 39. | CH$_2$CH$_2$CH$_2$ | CH—CH$_2$ | 1 | 1 | 1 | S | Et | 6-F | p-phenol | H |

TABLE 1-continued

Examples according to formula EX1:

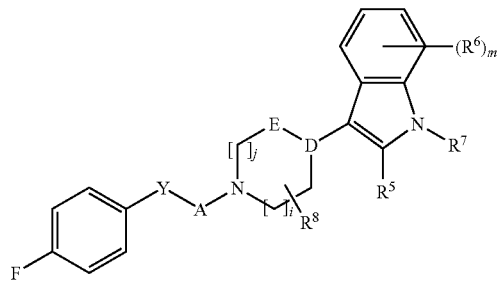

| # | A | D—E | i | j | m | Y | $R^5$ | $R^6$ | $R^7$ | $R^8$ |
|---|---|---|---|---|---|---|---|---|---|---|
| 40. | $CH_2CH_2CH_2$ | $CH-CH_2$ | 1 | 1 | 1 | S | Et | 6-F | 3,5-di-Fluoro-4-phenol | H |
| 41. | $CH_2CH_2CH_2$ | $CH-CH_2$ | 1 | 1 | 1 | O | Et | 6-F | p-benzoic acid ethyl ester | H |
| 42. | $CH_2CH_2CH_2$ | $CH-CH_2$ | 1 | 1 | 1 | O | Et | 6-F | p-benzoic acid | H |
| 43. | $CH_2CH_2CH_2$ | $CH-CH_2$ | 1 | 1 | 1 | S | $CO_2Et$ | 6-F | phenyl | H |
| 44. | $CH_2CH_2CH_2$ | $CH-CH_2$ | 1 | 1 | 1 | S | $CO_2H$ | 6-F | phenyl | H |
| 45. | $CH_2CH_2CH_2$ | $CH-CH_2$ | 1 | 1 | 1 | S | $CH_2OH$ | 6-F | p-benzoic acid | H |
| 46. | $CH_2CH_2CH_2$ | $CH-CH_2$ | 1 | 1 | 1 | S | $OCH_3$ | 6-F | p-benzoic acid | H |
| 47. | $CH_2CH_2CH_2$ | $CH-CH_2$ | 1 | 1 | 1 | S | tetrazole | 6-F | phenyl | H |
| 48. | $CH_2CH_2CH_2$ | $CH-CH_2$ | 1 | 1 | 1 | S | $CH_2OH$ | 6-F | p-benzoic acid ethyl ester | H |
| 49. | $CH_2CH_2CH_2$ | $CH-CH_2$ | 1 | 1 | 1 | S | $OCH_3$ | 6-F | p-benzoic acid ethyl ester | H |
| 50. | $CH_2CH_2CH_2$ | $CH-CH_2$ | 2 | 0 | 1 | S | Et | 6-F | phenyl | 4-F** |
| 51. | $CH_2CH_2CH_2$ | $CH-CH_2$ | 2 | 0 | 1 | S | Et | 6-F | phenyl | 4-OH |
| 52. | $CH_2CH_2CH_2$ | $CH-CH_2$ | 1 | 1 | 0 | S | Et | — | phenyl | 4-OH |
| 53. | $CH_2CH_2CH_2$ | $CH-CH_2$ | 2 | 0 | 1 | S | Et | 6-F | phenyl | 4,4-di-F |
| 54. | $CH_2CH_2CH_2$ | $CH-CH_2$ | 1 | 1 | 1 | S | Et | 6-F | phenyl | H |
| 55. | $CH_2CF_2CH_2$ | $CH-CH_2$ | 1 | 1 | 1 | S | Et | 6-F | phenyl | H |
| 56. | $CH_2CH(CH_2OH)CH_2$ | $CH-CH_2$ | 1 | 1 | 1 | S | Et | 6-F | phenyl | H |
| 57. | $CH_2CH_2CH_2$ | $C-CH_2$ | 1 | 1 | 1 | S | Et | 6-F | phenyl | 4-F*** |
| 58. | $CH_2CH_2CH_2$ | $C-CH_2$ | 1 | 1 | 1 | S | Et | 6-F | p-methoxyphenyl | H |
| 59. | $CH_2CH_2CH_2$ | $C-CH_2$ | 1 | 1 | 1 | S | Et | 6-F | p-benzoic acid methyl ester | H |
| 60. | $CH_2CH_2CH_2$ | $C-CH_2$ | 1 | 1 | 1 | S | Et | 6-F | p-benzoic acid ethyl ester | H |
| 61. | $CH_2CH_2CH_2$ | $C-CH_2$ | 1 | 1 | 1 | S | Et | 6-F | m-flouro-p-benzoic acid ethyl ester | H |
| 62. | $CH_2CH_2CH_2$ | $C-CH_2$ | 1 | 1 | 0 | S | Et | — | m-methyl-p-benzoic acid ethyl ester | H |
| 63. | $CH_2CH_2CH_2$ | $C-CH_2$ | 1 | 1 | 0 | S | Et | — | o-nitro-p-benzoic acid | H |
| 64. | $CH_2CH_2CH_2$ | $C-CH_2$ | 1 | 1 | 1 | S | Et | 6-F | m-flouro-p-benzoic acid | H |
| 65. | $CH_2CH_2CH_2$ | $C-CH_2$ | 1 | 1 | 1 | S | Et | 6-F | p-phenyl acetic acid | H |
| 66. | $CH_2CH_2CH_2$ | $C-CH_2$ | 1 | 1 | 0 | S | Et | — | m-methyl-p-benzoic acid ethyl ester | H |
| 67. | $CH_2CH_2CH_2$ | $C-CH_2$ | 1 | 1 | 1 | S | Et | 6-F | p-benzoic acid propyl ester | H |
| 68. | $CH_2CH_2CH_2$ | $C-CH_2$ | 1 | 1 | 1 | S | Et | 6-F | p-benzoic acid butyl ester | H |
| 69. | $CH_2CH_2CH_2$ | $C-CH_2$ | 1 | 1 | 1 | S | Et | 6-F | p-benzoic acid pentyl ester | H |
| 70. | $CH_2CH_2CH_2$ | $C-CH_2$ | 1 | 1 | 1 | S | Et | 6-COOEt | phenyl | H |
| 71. | $CH_2CH_2CH_2$ | $C-CH_2$ | 1 | 1 | 1 | NH | Et | 6-F | p-benzoic acid ethyl ester | H |
| 72. | $CH_2CH_2CH_2$ | $C-CH_2$ | 1 | 1 | 1 | O | Et | 6-F | p-benzoic acid ethyl ester | H |
| 73. | $CH_2CH_2CH_2$ | $C-CH_2$ | 1 | 1 | 1 | NH | Et | 6-F | p-benzoic acid | H |
| 74. | $CH_2CH_2CH_2$ | $C-CH_2$ | 1 | 1 | 1 | $CH_2$ | Et | 6-F | p-benzoic acid ethyl ester | H |
| 75. | $CH_2CH_2CH_2$ | $C-CH_2$ | 1 | 1 | 1 | $CH_2$ | Et | 6-F | p-benzoic acid | H |

*p-S(O)NHR-phenyl;

**4- = from piperidino N;

***4- = attached to atom D

TABLE 2

Examples according to formula EX2

EX2

| # | A | D—E | i | j | m | Y | $R^{2a}$ | $R^{2b}$ | $R^6$ | $R^7$ |
|---|---|---|---|---|---|---|---|---|---|---|
| 76. | $CH_2CH_2CH_2$ | CH—$CH_2$ | 1 | 1 | 1 | S | Cl | H | 6-F | p-benzoic acid ethyl ester |
| 77. | $CH_2CH_2CH_2$ | CH—$CH_2$ | 1 | 1 | 1 | S | Cl | H | 6-F | p-benzoic acid |
| 78. | $CH_2CH_2CH_2$ | CH—$CH_2$ | 1 | 1 | 0 | S | Cl | Cl | — | p-benzoic acid methyl ester |
| 79. | $CH_2CH_2CH_2$ | CH—$CH_2$ | 1 | 1 | 0 | S | Cl | Cl | — | p-benzoic acid |

Method of Treatment

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, survival or proliferation of CCR-3 expressing cells is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays.

Similarly, an instant compound which promotes one or more functions of the mammalian chemokine receptor (e.g., a human chemokine) as administered to stimulate (induce or enhance) survival or proliferation of CCR-3 expressing cells or an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversushost disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., Anisaki sp., Phocanema sp.), cutaneous larva migraines (Ancylostona braziliense, Ancylostoma caninum). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combinations

The compounds of general formula 1 may be used on their own or combined with other active substances of formula 1 according to the invention. The compounds of general formula 1 may optionally also be combined with other pharmacologically active substances. These include, in particular, betamimetics, anticholinergics, corticosteroids, PDE4-inhibitors, LTD4-antagonists, EGFR-inhibitors, dopamin-agonists, antiallergic agents, PAF-antagonists und PI3-kinase inhibitors, but also combinations of two or three active substances, i.e:

Betamimetics with corticosteroids, PDE4-inhibitors, EGFR-inhibitors or LTD4-antagonists, Anticholinergics with betamimetics, corticosteroids, PDE4-inhibitors, EGFR-inhibitors or LTD4-antagonists, Corticosteroids with PDE4-inhibitors, EGFR-inhibitors or LTD4-antagonists PDE4-inhibitors with EGFR-inhibtors or LTD4-antagonists EGFR-inhibtors with LTD4-antagonists.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, CHF-1035, HOKU-81, KUL-1248 and 3-(4-{6-[2-Hydroxy-2-(4-hydroxy-3-hydroxymethylphenyl)-ethylamino]-hexyloxy}-butyl)-benzyl-sulfonamide 5-[2-(5,6-Diethyl-indan-2-ylamino)-1-hydroxy-ethyl]-8-hydroxy-1H-quinolin-2-one 4-Hydroxy-7-[2-{[2-{[3-(2-phenylethoxy)propyl]sulphonyl}ethyl]-amino}ethyl]-2(3H)-benzothiazolone 1-(2-Fluoro-4-hydroxyphenyl)-2-[4-(1-benzimidazolyl)-2-methyl-2-butylamino]ethanole 1-[3-(4-Methoxybenzyl-amino)-4-hydroxyphenyl]-2-[4-(1-benzimidazolyl)-2-methyl-2-butylamino]ethanole 1-[2H-5-hydroxy-3-oxo-4H-1,4-benzoxazin-8-yl]-2-[3-(4-N,N-dimethylaminophenyl)-2-methyl-2-propylamino]ethanole 1-[2H-5-hydroxy-3-oxo-4H-1,4-benzoxazin-8-yl]-2-[3-(4-methoxyphenyl)-2-methyl-2-propylamino]ethanole 1-[2H-5-hydroxy-3-oxo-4H-1,4-benzoxazin-8-yl]-2-[3-(4-n-butyloxyphenyl)-2-methyl-2-propylamino]ethanole 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-Hydroxy-8-(1-hydroxy-2-isopropylaminobutyl)-2H-1,4-benzoxazin-3-(4H)-one 1-(4-Amino-3-chloro-5-trifluormethylphenyl)-2-tert.-butylamino)ethanol 6-Hydroxy-8-{1-hydroxy-2-[2-(4-methoxy-phenyl)-1,1-dimethyl-ethylamino]-ethyl}-4H-benzo[1,4]oxazin-3-one 6-Hydroxy-8-{1-hydroxy-2-[2-(4-phenoxy-acetic acid ethylester)-1,1-dimethyl-ethylamino]-ethyl}-4H-benzo[1,4]oxazin-3-one 6-Hydroxy-8-{1-hydroxy-2-[2-(4-phenoxy-acetic acid)-1,1-dimethyl-ethylamino]-ethyl}-4H-benzo[1,4]oxazin-3-one 8-{2-[, 1-Dimethyl-2-(2,4,6-tri methyl phenyl)-ethylamino]-1-hydroxy-ethyl}-6-hydroxy-4H-benzo[1,4]oxazin-3-one 6-Hydroxy-8-{1-hydroxy-2-[2-(4-hydroxy-phenyl)-1,1-dimethyl-ethylamino]-ethyl}-4H-benzo[1,4]oxazin-3-one 6-Hydroxy-8-{1-hydroxy-2-[2-(4-isopropyl-phenyl)-1,1 dimethyl-ethylamino]-ethyl}-4H-benzo[1,4]oxazin-3-one 8-{2-[2-(4-Ethyl-phenyl)-1,1-dimethyl-ethylamino]-1-hydroxy-ethyl}-6-hydroxy-4H-benzo[1,4]oxazin-3-one 8-{2-[2-(4-Ethoxy-phenyl)-1,1-dimethyl-ethylamino]-1-hydroxy-ethyl}-6-hydroxy-4H-benzo[1,4]oxazin-3-one 4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-Difluor-phenyl)-1,1-dimethyl-ethylamino]-1-hydroxy-ethyl}-6-hydroxy-4H-benzo[1,4]oxazin-3-on 1-(4-Ethoxy-carbonylamino-3-cyano-5-fluorophenyl)-2-(tert.-butylamino)ethanol optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Glycopyrronium salts, preferred the bromide salt, Trospium salts, preferred the chloride salt, Tolterodin. From the above mentioned salts the pharmacologically active part is the cation, possible anions are chloride, bromide, iodide, sulfate, phosphate, methansulfonate, nitrate, maleate, acetate, citrate, fumarate, tartrate, oxalate, succinate, benzoate oder p-toluenesulfonate. Furthermore 2,2-Diphenylpropion acid tropenolester-methobromide
2,2-Diphenylpropion acid scopinester-methobromide
2-Fluor-2,2-Diphenylacetic acid scopinester-methobromide 2-Fluor-2,2-Diphenylacetic acid tropenolester-methobromide 3,3',4,4'-Tetrafluorbenzil acid tropenolester-Methobromide 3,3',4,4'-Tetrafluorbenzil acid scopinester-Methobromide 4,4'-Difluorbenzil acid tropenolester-Methobromide 4,4'-Difluorbenzil acid scopinester-Methobromide 3,3'-Difluorbenzil acid tropenolester-Methobromide 3,3'-Difluorbenzil acid scopinester-Methobromide9-Hydroxy-fluoren-9-carbon acid tropenolester-Methobromide 9-Fluor-fluoren-9-carbon acid tropenolester-Methobromide 9-Hydroxy-fluoren-9-carbon acid scopinester-Methobromide 9-Fluor-fluoren-9-carbon acid scopinester Methobromide 9-Methyl-fluoren-9-carbon acid tropenolesterMethobromide 9-Methyl-fluoren-9-carbon acid scopinesterMethobromide Benzil acid cyclopropyltropinester-Methobromide 2,2-Diphenylpropion acid cyclopropyltropinester-Methobromide 9-Hydroxy-xanthen-9-carbon acid cyclopropyltropinesterMethobromide 9-Methyl-fluoren-9-carbon acid cyclopropyltropinester-Methobromide 9-Methyl-xanthen-9-carbon acid cyclopropyltropinester-Methobromide 9-Hydroxy-fluoren-9-carbon acid cyclopropyltropinester-Methobromide 4,4'-Difluorbenzil acid methylestercyclopropyltropinester-Methobromide 9-Hydroxy-xanthen-9-carbon acid tropenolester-Methobromide 9-Hydroxy-xanthen-9-carbon acid scopinester Methobromide 9-Methyl-xanthen-9-carbon acid tropenolester-Methobromide 9-Methyl-xanthen-9-carbon acid scopinesterMethobromide 9-Ethyl-xanthen-9-carbon acid tropenolester Methobromide 9-Difluormethyl-xanthen-9-carbon acid tropenolester-Methobromide 9-Hydroxymethyl-xanthen-9-carbon acid scopinester-Methobromide Examples of preferred corticosteroids which may be mentioned include Prednisolone, Prednisone, Butixocortpropionate, Flunisolide, Beclomethasone, Triamcinolone, Budesonide, Fluticasone, Mometasone, Ciclesonide, Rofleponide, Dexamethasone, Betamethasone, Deflazacorte, RPR-106541, NS-126, ST-26 and 6,9-Difluoro-17-[(2-furanylcarbonyl)oxy]-11-hydroxy-16-methyl-3-oxo-androsta-1,4-dien-17-carbothion acid (S)-fluoromethylester 6,9-Difluoro-11-hydroxy-16-methyl-3-oxo-17-propionyloxy-androsta-1,4-dien-17-carbothion acid (S)-(2-oxo-tetrahydro-furan-3S-yl)ester, Etiprednole-dichloroacetat optionally in racemic form, as enantiomers, diastereomeres or as pharmacologically acceptable salts, solvates or hydrates. Examples for preferred salts and derivatives are alkali salts, i.e. sodium or potassium salts, sulfobenzoates, phosphates, isonicotinates, acetates, propionates, dihydrogenphosphates, palmitates, pivalates or furoates.

Examples of preferred PDE4-inhibitors which may be mentioned include Enprofylline, Theophylline, Roflumilaste, Ariflo (Cilomilast), Tofimilaste, Pumafentrine, Lirimilaste, Arofylline, Atizorame, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-Dichloro-1-oxo-pyridin-4-yl)-4-difluoromethoxy-3-cyclopropylmethoxy-benzamide (−)p-[(4aR*, 10bS*)-9-Ethoxy-1,2,3,4,4a, 10b-hexahydro-8-methoxy-2-methylbenzo[s][1,6]naphthyridin-6-yl]-N,N-diisopropylbenzamid (R)-(+)-1-(4-Bromobenzyl)-4-[(3-cyclopentyloxy)-4-methoxyphenyl]-2-pyrrolidon 3-(Cyclopentyloxy-4-methoxyphenyl)-1-(4-N'-[N-2-cyano-S-methyl-isothioureido]benzyl)-2-pyrrolidone cis[4-Cyano-4-(3-cyclopentyloxy-4-methoxyphenyl)cyclohexan-1-carbon acid]

2-carbomethoxy-4-cyano-4-(3-cyclopropylmethoxy-4-difluoromethoxy-phenyl)cyclohexan-1-one cis[4-Cyano-4-(3-cyclopropylmethoxy-4-difluoromethoxyphenyl)cyclohexan-1-ol]

(R)-(+)-Ethyl[4-(3-cyclopentyloxy-4-methoxyphenyl)pyrrolidin-2-yliden]acetate (S)-(–)-Ethyl[4-(3-cyclopentyloxy-4-methoxyphenyl)
pyrrolidin-2-yliden]acetate
9-Cyclopentyl-5,6-dihydro-7-ethyl-3-(2-thienyl)-9H-
pyrazolo[3,4-c]-1,2,4-triazolo[4,3-a]pyridine
9-Cyclopentyl-5,6-dihydro-7-ethyl-3-(tert-butyl)-9H-
pyrazolo[3,4-c]-1,2,4-triazolo[4,3-a]pyridine optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred LTD4-antagonists which may be mentioned include Montelukaste, Pranlukaste, Zafirlukaste, MCC-847 (ZD-3523), MN-001, MEN-91507 (LM-1507), VUF-5078, VUF-K-8707, L-733321 and 1-(((R)-(3-(2-(6,7-Difluoro-2-quinolinyl)ethenyl)phe-
nyl)-3-(2-(2-hydroxy-2-propyl)phenyl)thio)methylcy-
clopropane-acetic acid,
1-(((1 (R)-3(3-(2-(2,3-Dichlorothieno[3,2-b]pyridin-5-
yl)-(E)-ethenyl)phenyl)-3-(2-(1-hydroxy-1-methyl-
ethyl)phenyl)propyl)thio)methyl)cyclopropane acetic
acid
[2-[[2-(4-tert-Butyl-2-thiazolyl)-5-benzofuranyl]oxym-
ethyl]phenyl]acetic acid optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate. Further examples for optionally preferred salts and derivatives are alkali salts, i.e. sodium or potassium salts, sulfobenzoates, phosphates, isonicotinates, acetates, propionates, di hydrogen phosphates, palmitates, pivalates or furoates.

Examples of preferred EGFR-inhibitors which may be mentioned include Cetuximabe, Trastuzumabe, ABX-EGF, Mab ICR-62 and 4-[(3-Chlor-4-fluorphenyl)amino]-6-{[4-(morpholin-4-
yl)-1-oxo-2-buten-1-yl]amino}-7-cyclopropyl-
methoxy-chinazoline
4-[(3-Chlor-4-fluorphenyl)amino]-6-{[4-(N,N-diethy-
lamino)-1-oxo-2-buten-1-yl]amino}-7-cyclopropyl-
methoxy-chinazoline
4-[(3-Chlor-4-fluorphenyl)amino]-6-{[4-(N,N-dimethy-
lamino)-1-oxo-2-buten-1-yl]amino}-7-cyclopropyl-
methoxy-chinazoline
4-[(R)-(1-Phenyl-ethyl)amino]-6-{[4-(morpholin-4-yl)-
1-oxo-2-buten-1-yl]amino}-7-cyclopentyloxy-china-
zoline
4-[(3-Chlor-4-fluor-phenyl)amino]-6-{[4-((R)-6-methyl-
2-oxo-morpholin-4-yl)-1-oxo-2-buten-1-yl]amino}-7-
cyclopropylmethoxy-chinazoline
4-[(3-Chlor-4-fluor-phenyl)amino]-6-{[4-((R)-6-methyl-
2-oxo-morpholin-4-yl)-1-oxo-2-buten-1-yl]amino}-7-
[(S)-(tetrahydrofuran-3-yl)oxy]-chinazoline
4-[(3-Chlor-4-fluor-phenyl)amino]-6-{[4-((R)-2-meth-
oxymethyl-6-oxo-morpholin-4-yl)-1-oxo-2-buten-1-
yl]amino}-7-cyclopropylmethoxy-chinazoline
4-[(3-Chlor-4-fluor-phenyl)amino]-6-[2-((S)-6-methyl-2-
oxo-morpholin-4-yl)-ethoxy]-7-methoxy-chinazoline
4-[(3-Chlor-4-fluorphenyl)amino]-6-({4-[N-(2-methoxy-
ethyl)-N-methyl-amino]-1-oxo-2-buten-1-yl}amino)-
7-cyclopropyl methoxy-chinazoline
4-[(3-Chlor-4-fluorphenyl)amino]-6-{[4-(N,N-dimethy-
lamino)-1-oxo-2-buten-1-yl]amino}-7-cyclopenty-
loxy-chinazoline
4-[(R)-(1-Phenyl-ethyl)amino]-6-{[4-(N,N-bis-(2-meth-
oxy-ethyl)-amino)-1-oxo-2-buten-1-yl]amino}-7-cy-
clopropylmethoxy-chinazoline
4-[(R)-(1-Phenyl-ethyl)amino]-6-({4-[N-(2-methoxy-
ethyl)-N-ethyl-amino]-1-oxo-2-buten-1-yl}amino)-7-
cyclopropyl methoxy-chinazoline
4-[(R)-(1-Phenyl-ethyl)amino]-6-({4-[N-(2-methoxy-
ethyl)-N-methyl-amino]-1-oxo-2-buten-1-yl}amino)-
7-cyclopropyl methoxy-chinazoline
4-[(R)-(1-Phenyl-ethyl)amino]-6-({4-[N-(tetrahydropy-
ran-4-yl)-N-methyl-amino]-1-oxo-2-buten-1-
yl}amino)-7-cyclopropylmethoxy-chinazoline
4-[(3-Chlor-4-fluorphenyl)amino]-6-{[4-(N,N-dimethy-
lamino)-1-oxo-2-buten-1-yl]amino}-7-((R)-tetrahydro-
furan-3-yloxy)-chinazoline
4-[(3-Chlor-4-fluorphenyl)amino]-6-{[4-(N,N-dimethy-
lamino)-1-oxo-2-buten-1-yl]amino}-7-((S)-tetrahydro-
furan-3-yloxy)-chinazoline
4-[(3-Chlor-4-fluorphenyl)amino]-6-({4-[N-(2-methoxy-
ethyl)-N-methyl-amino]-1-oxo-2-buten-1-yl}amino)-
7-cyclopentyloxy-chinazoline
4-[(3-Chlor-4-fluorphenyl)amino]-6-{[4-(N-cyclopropyl-
N-methyl-amino)-1-oxo-2-buten-1-yl]amino}-7-cyclo-
pentyloxy-chinazoline
4-[(3-Chlor-4-fluorphenyl)amino]-6-{[4-(N,N-dimethy-
lamino)-1-oxo-2-buten-1-yl]amino}-7-[(R)-(tetrahy-
drofuran-2-yl)methoxy]-chinazoline
4-[(3-Chlor-4-fluorphenyl)amino]-6-{[4-(N,N-dimethy-
lamino)-1-oxo-2-buten-1-yl]amino}-7-[(S)-(tetrahy-
drofuran-2-yl)methoxy]-chinazoline
4-[(3-Ethinyl-phenyl)amino]-6,7-bis-(2-methoxy-
ethoxy)-chinazoline
4-[(3-Chlor-4-fluorphenyl)amino]-7-[3-(morpholin-4-
yl)-propyloxy]-6-[(vinyl-carbonyl)amino]-chinazoline
4-[(R)-(1-Phenyl-ethyl)amino]-6-(4-hydroxy-phenyl)-
7H-pyrrolo[2,3-d]pyrimidine
3-Cyano-4-[(3-chlor-4-fluorphenyl)amino]-6-{[4-(N,N-
dimethylamino)-1-oxo-2-buten-1-yl]amino}-7-ethoxy-
chinazoline
4-{[3-Chlor-4-(3-fluor-benzyloxy)-phenyl]amino}-6-(5-{
[(2-methansulfonyl-ethyl)amino]methyl}-furan-2-yl)
chinazoline
4-[(R)-(1-Phenyl-ethyl)amino]-6-{[4-((R)-6-methyl-2-
oxo-morpholin-4-yl)-1-oxo-2-buten-1-yl]amino}-7-
methoxy-chinazoline
4-[(3-Chlor-4-fluorphenyl)amino]-6-{[4-(morpholin-4-
yl)-1-oxo-2-buten-1-yl]amino}-7-[(tetrahydrofuran-2-
yl)methoxy]-chinazoline
4-[(3-Chlor-4-fluorphenyl)amino]-6-({4-[N,N-bis-(2-
methoxy-ethyl)-amino]-1-oxo-2-buten-1-yl}amino)-7-
[(tetrahydrofuran-2-yl)methoxy]-chinazoline
4-[(3-Ethinyl-phenyl)amino]-6-{[4-(5,5-dimethyl-2-oxo-
morpholin-4-yl)-1-oxo-2-buten-1-yl]amino}-chinazo-
line
4-[(3-Chlor-4-fluor-phenyl)amino]-6-[2-(2,2-dimethyl-6-
oxo-morpholin-4-yl)-ethoxy]-7-methoxy-chinazoline
4-[(3-Chlor-4-fluor-phenyl)amino]-6-[2-(2,2-dimethyl-6-
oxo-morpholin-4-yl)-ethoxy]-7-[(R)-(tetrahydrofuran-
2-yl)methoxy]-chinazoline 4-[(3-Chlor-4-fluor-phenyl)amino]-7-[2-(2,2-dimethyl-6-oxo-morpholin-4-yl)-ethoxy]-6-[(S)-(tetrahydrofuran-2-yl)methoxy]-chinazoline 4-[(3-Chlor-4-fluor-phenyl)amino]-6-{2-[4-(2-oxo-morpholin-4-yl)-piperidin-1-yl]-ethoxy}-7-methoxy-chinazoline 4-[(3-Chlor-4-fluor-phenyl)amino]-6-[1-(tert.-butyloxycarbonyl)-piperidin-4-yloxy]-7-methoxy-chinazoline 4-[(3-Chlor-4-fluor-phenyl)amino]-6-(trans-4-amino-cyclohexan-1-yloxy)-7-methoxy-chinazoline 4-[(3-Chlor-4-fluor-phenyl)amino]-6-(trans-4-methansulfonylamino-cyclohexan-1-yloxy)-7-methoxy-chinazoline 4-[(3-Chlor-4-fluor-phenyl)amino]-6-(tetrahydropyran-3-yloxy)-7-methoxy-chinazoline 4-[(3-Chlor-4-fluor-phenyl)amino]-6-(1-methyl-piperidin-4-yloxy)-7-methoxy-chinazoline 4-[(3-Chlor-4-fluor-phenyl)amino]-6-{1-[(morpholin-4-yl)carbonyl]-piperidin-4-yloxy}-7-methoxy-chinazoline 4-[(3-Chlor-4-fluor-phenyl)amino]-6-{1-[(methoxymethyl)carbonyl]-piperidin-4-yloxy}-7-methoxy-chinazoline 4-[(3-Chlor-4-fluor-phenyl)amino]-6-(piperidin-3-yloxy)-7-methoxy-chinazoline 4-[(3-Chlor-4-fluor-phenyl)amino]-6-[1-(2-acetylamino-ethyl)-piperidin-4-yloxy]-7-methoxy-chinazoline 4-[(3-Chlor-4-fluor-phenyl)amino]-6-(tetrahydropyran-4-yloxy)-7-ethoxy-chinazoline 4-[(3-Chlor-4-fluor-phenyl)amino]-6-((S)-tetrahydrofuran-3-yloxy)-7-hydroxy-chinazoline 4-[(3-Chlor-4-fluor-phenyl)amino]-6-(tetrahydropyran-4-yloxy)-7-(2-methoxy-ethoxy)-chinazoline 4-[(3-Chlor-4-fluor-phenyl)amino]-6-{trans-4-[(dimethylamino)sulfonylamino]-cyclohexan-1-yloxy}-7-methoxy-chinazoline 4-[(3-Chlor-4-fluor-phenyl)amino]-6-{trans-4-[(morpholin-4-yl)carbonylamino]-cyclohexan-1-yloxy}-7-methoxy-chinazoline 4-[(3-Chlor-4-fluor-phenyl)amino]-6-{trans-4-[(morpholin-4-yl)sulfonylamino]-cyclohexan-1-yloxy}-7-methoxy-chinazoline 4-[(3-Chlor-4-fluor-phenyl)amino]-6-(tetrahydropyran-4-yloxy)-7-(2-acetylamino-ethoxy)-chinazoline 4-[(3-Chlor-4-fluor-phenyl)amino]-6-(tetrahydropyran-4-yloxy)-7-(2-methansulfonylamino-ethoxy)-chinazoline 4-[(3-Chlor-4-fluor-phenyl)amino]-6-{1-[(piperidin-1-yl)carbonyl]-piperidin-4-yloxy}-7-methoxy-chinazoline 4-[(3-Chlor-4-fluor-phenyl)amino]-6-(1-aminocarbonylmethyl-piperidin-4-yloxy)-7-methoxy-chinazoline 4-[(3-Chlor-4-fluor-phenyl)amino]-6-(cis-4-{N-[(tetrahydropyran-4-yl)carbonyl]-N-methyl-amino}-cyclohexan-1-yloxy)-7-methoxy-chinazoline 4-[(3-Chlor-4-fluor-phenyl)amino]-6-(cis-4-{N-[(morpholin-4-yl)carbonyl]-N-methyl-amino}-cyclohexan-1-yloxy)-7-methoxy-chinazoline 4-[(3-Chlor-4-fluor-phenyl)amino]-6-(cis-4-{N-[(morpholin-4-yl)sulfonyl]-N-methyl-amino}-cyclohexan-1-yloxy)-7-methoxy-chinazoline 4-[(3-Chlor-4-fluor-phenyl)amino]-6-(trans-4-ethansulfonylamino-cyclohexan-1-yloxy)-7-methoxy-chinazoline 4-[(3-Chlor-4-fluor-phenyl)amino]-6-(1-methansulfonyl-piperidin-4-yloxy)-7-ethoxy-chinazoline 4-[(3-Chlor-4-fluor-phenyl)amino]-6-(1-methansulfonyl-piperidin-4-yloxy)-7-(2-methoxy-ethoxy)-chinazoline 4-[(3-Chlor-4-fluor-phenyl)amino]-6-[1-(2-methoxy-acetyl)-piperidin-4-yloxy]-7-(2-methoxy-ethoxy)-chinazoline 4-[(3-Chlor-4-fluor-phenyl)amino]-6-(cis-4-acetylamino-cyclohexan-1-yloxy)-7-methoxy-chinazoline 4-[(3-Ethinyl-phenyl)amino]-6-[1-(tert.-butyloxycarbonyl)-piperidin-4-yloxy]-7-methoxy-chinazoline 4-[(3-Ethinyl-phenyl)amino]-6-(tetrahydropyran-4-yloxy]-7-methoxy-chinazoline 4-[(3-Chlor-4-fluor-phenyl)amino]-6-(cis-4-{N-[(piperidin-1-yl)carbonyl]-N-methyl-amino}-cyclohexan-1-yloxy)-7-methoxy-chinazoline 4-[(3-Chlor-4-fluor-phenyl)amino]-6-(cis-4-{N-[(4-methyl-piperazin-1-yl)carbonyl]-N-methyl-amino}-cyclohexan-1-yloxy)-7-methoxy-chinazoline 4-[(3-Chlor-4-fluor-phenyl)amino]-6-{cis-4-[(morpholin-4-yl)carbonylamino]-cyclohexan-1-yloxy}-7-methoxy-chinazoline 4-[(3-Chlor-4-fluor-phenyl)amino]-6-{1-[2-(2-oxopyrrolidin-1-yl)ethyl]-piperidin-4-yloxy}-7-methoxy-chinazoline 4-[(3-Chlor-4-fluor-phenyl)amino]-6-{1-[(morpholin-4-yl)carbonyl]-piperidin-4-yloxy}-7-(2-methoxy-ethoxy)-chinazoline 4-[(3-Ethinyl-phenyl)amino]-6-(1-acetyl-piperidin-4-yloxy)-7-methoxy-chinazoline 4-[(3-Ethinyl-phenyl)amino]-6-(1-methyl-piperidin-4-yloxy)-7-methoxy-chinazoline 4-[(3-Ethinyl-phenyl)amino]-6-(1-methansulfonyl-piperidin-4-yloxy)-7-methoxy-chinazoline 4-[(3-Chlor-4-fluor-phenyl)amino]-6-(1-methyl-piperidin-4-yloxy)-7(2-methoxy-ethoxy)-chinazoline 4-[(3-Chlor-4-fluor-phenyl)amino]-6-(1-isopropyloxycarbonyl-piperidin-4-yloxy)-7-methoxy-chinazoline 4-[(3-Chlor-4-fluor-phenyl)amino]-6-(cis-4-methylamino-cyclohexan-1-yloxy)-7-methoxy-chinazoline 4-[(3-Chlor-4-fluor-phenyl)amino]-6-{cis-4-[N-(2-methoxy-acetyl)-N-methyl-amino]-cyclohexan-1-yloxy}-7-methoxy-chinazoline 4-[(3-Ethinyl-phenyl)amino]-6-(piperidin-4-yloxy)-7-methoxy-chinazoline 4-[(3-Ethinyl-phenyl)amino]-6-[1-(2-methoxy-acetyl)-piperidin-4-yloxy]-7-methoxy-chinazoline 4-[(3-Ethinyl-phenyl)amino]-6-{1-[(morpholin-4-yl)carbonyl]-piperidin-4-yloxy}-7-methoxy-chinazoline 4-[(3-Chlor-4-fluor-phenyl)amino]-6-{1-[(cis-2,6-dimethyl-morpholin-4-yl)carbonyl]-piperidin-4-yloxy}-7-methoxy-chinazoline 4-[(3-Chlor-4-fluor-phenyl)amino]-6-{1-[(2-methyl-morpholin-4-yl)carbonyl]-piperidin-4-yloxy}-7-methoxy-chinazoline 4-[(3-Chlor-4-fluor-phenyl)amino]-6-{1-[(S,S)-(2-oxa-5-aza-bicyclo[2.2.1]hept-5-yl)carbonyl]-piperidin-4-yloxy}-7-methoxy-chinazoline 4-[(3-Chlor-4-fluor-phenyl)amino]-6-{1-[(N-methyl-N-2-methoxyethyl-amino)carbonyl]-piperidin-4-yloxy}-7-methoxy-chinazoline 4-[(3-Chlor-4-fluor-phenyl)amino]-6-(1-ethyl-piperidin-4-yloxy)-7-methoxy-chinazoline 4-[(3-Chlor-4-fluor-phenyl)amino]-6-{1-[(2-methoxyethyl)carbonyl]-piperidin-4-yloxy}-7-methoxy-chinazoline 4-[(3-Chlor-4-fluor-phenyl)amino]-6-{1-[(3-methoxypropyl-amino)-carbonyl]-piperidin-4-yloxy}-7-methoxy-chinazoline 4-[(3-Chlor-4-fluor-phenyl)amino]-6-[cis-4-(N-methansulfonyl-N-methyl-amino)-cyclohexan-1-yloxy]-7-methoxy-chinazoline 4-[(3-Chlor-4-fluor-phenyl)amino]-6-[cis-4-(N-acetyl-N-methyl-amino)-cyclohexan-1-yloxy]-7-methoxy-chinazoline 4-[(3-Chlor-4-fluor-phenyl)amino]-6-(trans-4-methylamino-cyclohexan-1-yloxy)-7-methoxy-chinazoline 4-[(3-Chlor-4-fluor-phenyl)amino]-6-[trans-4-(N-methansulfonyl-N-methyl-amino)-cyclohexan-1-yloxy]-7-methoxy-chinazoline 4-[(3-Chlor-4-fluor-phenyl)amino]-6-(trans-4-dimethylamino-cyclohexan-1-yloxy)-7-methoxy-chinazoline 4-[(3-Chlor-4-fluor-phenyl)amino]-6-(trans-4-{N-[(morpholin-4-yl)carbonyl]-N-methyl-amino}-cyclohexan-1-yloxy)-7-methoxy-chinazoline 4-[(3-Chlor-4-fluor-phenyl)amino]-6-[2-(2,2-dimethyl-6-oxo-morpholin-4-yl)-ethoxy]-7-[(S)-(tetrahydrofuran-2-yl)methoxy]-chinazoline 4-[(3-Chlor-4-fluor-phenyl)amino]-6-(1-methansulfonyl-piperidin-4-yloxy)-7-methoxy-chinazoline 4-[(3-Chlor-4-fluor-phenyl)amino]-6-(1-cyano-piperidin-4-yloxy)-7-methoxy-chinazoline optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred dopamin antagonists which may be mentioned include Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Desloratidine and Meclozine, optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Examples of preferred PAF antagonists which may be mentioned include 4-(2-Chlorphenyl)-9-methyl-2-[3(4-morpholinyl)-3-propanon-1-yl]-6H-thieno-[3,2-f]-[1,2,4]triazolo[4,3-a][1,4]diazepine 6-(2-Chlorphenyl)-8,9-dihydro-1-methyl-8-[(4-morpholinyl)carbonyl]-4H, 7H-cyclo-penta-[4,5]thieno-[3,2-f][1,2,4]triazolo[4,3-a][1,4]diazepine optionally in racemic form, as enantiomers, diastereomeres or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate und hydro-p-toluenesulfonate.

Pharmaceutical Forms

The compounds of formula 1 are administered to a mammal in a therapeutically effective amount. By "therapeutically effective amount" it is meant an amount of a compound of formula 1 that, when administered alone or in combination with an additional therapeutic agent to a mammal, is effective to prevent or ameliorate diseases, wherein the activity of a CCR-3-receptor is involved, or the progression of this disease.

Suitable preparations for administering the compounds of formula 1 include for example tablets, capsules, suppositories, solutions and powders etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

For administering the compounds of formula 1 it is particularly preferred according to the invention to use preparations or pharmaceutical formulations which are suitable for inhalation. Inhalable preparations include inhalable powders, propellant-containing metered-dose aerosols or propellant-free inhalable solutions. Within the scope of the present invention, the term propellant-free inhalable solutions also includes concentrates or sterile inhalable solutions ready for use. The formulations which may be used within the scope of the present invention are described in more detail in the next part of the specification.

The inhalable powders which may be used according to the invention may contain 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. It may sometimes seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred. Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the µg range. The compounds of formula 1 may also be used effectively above the µg range. The dosage may then be in the gram range, for example.

In another aspect the present invention relates to the above-mentioned pharmaceutical formulations as such which are characterised in that they contain a compound of formula 1, particularly the above-mentioned pharmaceutical formulations which can be administered by inhalation.

The following examples of formulations illustrate the present invention without restricting its scope:

EXAMPLES OF PHARMACEUTICAL FORMULATIONS

| A) Tablets | per tablet |
|---|---|
| active substance 1 | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the maize starch are mixed together. The mixture is screened, then moistened with a solution of polyvinylpyrrolidone in water, kneaded, wet granulated and dried. The granules, the remaining maize starch and the magnesium stearate are screened and mixed together. The mixture is pressed into tablets of suitable shape and size.

| B) Tablets | per tablet |
|---|---|
| active substance 1 | 80 mg |
| lactose | 55 mg |
| maize starch | 190 mg |
| microcrystalline cellulose | 35 mg |
| polyvinylpyrrolidone | 15 mg |
| sodium carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Ampoule solution | |
|---|---|
| active substance 1 | 50 mg |
| sodium chloride | 50 mg |
| water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilised and heat-sealed. The ampoules contain 5 mg, 25 mg and 50 mg of active substance.

| D) Metering aerosol | |
|---|---|
| active substance 1 | 0.005 |
| sorbitan trioleate | 0.1 |
| monofluorotrichloromethane and TG134a:TG227 2:1 | ad 100 |

The suspension is transferred into a conventional aerosol container with metering valve. Preferably 50 µl suspension are released on each actuation. The active substance may also be released in higher doses if desired (e.g. 0.02 wt.-%).

| E) Solutions (in mg/100 ml) | |
|---|---|
| active substance 1 | 333.3 mg |
| benzalkonium chloride | 10.0 mg |
| EDTA | 50.0 mg |
| HCl (1N) | ad pH 3.4 |

This solution can be prepared in the usual way.

| F) Inhalable powder | |
| --- | --- |
| active substance 1 | 12 μg |
| lactose monohydrate | ad 25 mg |

The inhalable powder is prepared in the usual way by mixing the individual ingredients.

We claim:

1. A compound of formula 1:

[Structure 1]

wherein $R^1$ is aryl, optionally substituted with one, two or three $R^2$;

$R^2$ are each independently $C_{1-6}$-alkyl, $C_{3-6}$-cycloalkyl, $C_{1-6}$-haloalkyl, $C_{6-10}$-aralkyl, halogen, CN, $COOR^3$, $COR^3$, $CONR^3R^4$, $NR^3R^4$, $NR^3SO_2R^4$, $OR^3$, $NO_2$, $SR^3$, $SOR^3$, $SO_2R^3$ or $SO_2NR^3R^4$;

$R^3$ is H, $C_{1-6}$-alkyl, $C_{3-8}$-cycloalkyl or ($-C_{3-8}$-cycloalkyl)-$C_{1-6}$-alkyl;

$R^4$ is H, $C_{1-6}$-alkyl, $C_{3-8}$-cycloalkyl or ($-C_{3-8}$-cycloalkyl)-$C_{1-6}$-alkyl;

$R^5$ is $C_{1-6}$-alkyl, $C_{1-6}$-alkoxy, $C_{1-6}$-acyloxy, $C_{6-10}$-aralkyl, $C_{3-6}$-cycloalkyl, ($C_{3-6}$-cycloalkyl)-$C_{1-6}$-alkyl, $C_{1-6}$-haloalkyl, $C_{1-6}$-thioalkyl, halogen, $NO_2$, CN, or $NR^3R^4$;

$R^6$ are each independently $C_{1-6}$-alkyl, $C_{1-6}$-alkoxy, $C_{1-6}$-acyloxy, $C_{6-10}$-aralkyl, $C_{3-6}$-cycloalkyl, $C_{1-6}$-haloalkyl, $C_{1-6}$-thioalkyl, halogen, $OR^3$, $SR^3$, CN, $NO_2$, $COOR^3$, $COR^3$, $CONR^3R^4$, $NR^3R^4$, $NR^3COR^4$, $NR^3SO_2R^4$, $SOR^3$, $SO_2R^3$, $SO_2NR^3R^4$, aryl or het;

$R^7$ is a substituent selected from the group consisting of aryl and het, both substituted with one, two, three or four substituents selected from the group consisting of $COOR^{7.1}$, $SO_2R^{7.1}$, $PO(OH)_2$, CONHCN, and $SO_2NHCOR^{7.1}$;

$R^{7.1}$ is H, $C_{1-6}$-alkyl or aryl;

$R^8$ is H, OH, $C_{1-6}$-alkoxy, $C_{1-6}$-haloalkyl, or halogen;

$R^9$ is H, OH, $C_{1-6}$-alkoxy, $C_{1-6}$-haloalkyl, or halogen;

A is straight, branched or cyclic $C_{2-8}$-alkylene; optionally substituted with $R^9$;

B is phenyl;

D-E is $-CH-CH_2-$, $-C=CH-$, $-^8-CH_2-$;

Y is $-CH_2-$, $-NR^4-$, $-O-$, $-S(O)_n-$;

i, j are each independently 0, 1 or 2, wherein i+j=2;

n is 0, 1 or 2;

m is 0, 1, 2, 3 or 4;

or a pharmaceutically acceptable salt thereof, with the proviso that both $R^7$ and $R^8$ cannot be hydrogen at the same time.

2. A compound of formula 1 according to claim 1, wherein Y is $-NR^4-$, $-O-$ or $-S(O)_n-$.

3. A compound according to claim 1, wherein $R^1$ is phenyl, optionally substituted with one, two or three $R^2$.

4. A compound according to claim 1, wherein $R^8$ is H.

5. A compound according to claim 1, wherein A is $-CH_2-CH_2-CH_2-$.

6. A compound according to claim 1, wherein $R^7$ is aryl or het, both optionally substituted with one, two, three or four substituents selected from the group consisting of $COOR^{7.1}$, $SO_2R^{7.1}$, $PO(OH)_2$, CONHCN, and $SO_2NHCOR^{7.1}$;

$R^{7.1}$ is H, $C_{1-6}$-alkyl or aryl;

and $R^8$ H.

7. A compound according to claim 1, wherein $R^5$ is $-C_{1-6}$-alkyl, $C_{3-6}$-cycloalkyl, or $C_{2-6}$-haloalkyl.

8. A compound according to claim 1, wherein $R^7$ is aryl, optionally substituted with one, two, three or four substituents selected from the group consisting of $COOR^{7.1}$, $SO_2R^{7.1}$, $PO(OH)_2$, CONHCN, and $SO_2NHCOH$; and $R^{7.1}$ H, $C_{1-6}$-alkyl or aryl.

9. A compound according to claim 1 of the following formula 1a:

[Structure 1a]

wherein $R^1$, $R^5$, $R^6$, $R^7$, $R^8$, A, B, Y and m are defined as in claim 1.

10. A compound of formula 1a according to claim 9, wherein:

$R^1$ is phenyl, optionally substituted with one, two or three $R^2$;

Y is $-NR^4-$, $-O-$ or $-S(O)_n-$;

A is $-CH_2-CH_2-CH_2-$;

$R^8$ is H;

$R^5$ is $-C_{1-6}$-alkyl, $C_{3-6}$-cycloalkyl, or $C_{2-6}$-haloalkyl;

$R^7$ is aryl, optionally substituted with one, two, three or four substituents selected from the group consisting of $COOR^{7.1}$, $SO_2R^{7.1}$, $PO(OH)_2$, CONHCN, and $SO_2NHCOH$;

$R^{7.1}$ H, $C_{1-6}$-alkyl or aryl; and

B is phenyl.

11. A compound of formula 1a according to claim 10, wherein:

$R^1$ is phenyl substituted by one or two halogen atoms.

12. A compound of formula 1a according to claim 10, wherein:

$R^7$ is phenyl, optionally substituted with one, two, three or four substituents selected from the group consisting of $COOR^{7.1}$, $SO_2R^{7.1}$, $PO(OH)_2$, CONHCN, and $SO_2NHCOH$.

13. A compound of formula 1a according to claim 11, wherein:

$R^7$ is phenyl, optionally substituted with one, two, three or four substituents selected from the group consisting of $COOR^{7.1}$, $SO_2R^{7.1}$, $PO(OH)_2$, CONHCN, and $SO_2NHCOH$.

14. A pharmaceutical composition comprising one or more compounds of formula 1 according to claim 1, and one or more pharmaceutically acceptable carriers or excipients.

* * * * *